(12) United States Patent
Dettke et al.

(10) Patent No.: US 11,564,943 B2
(45) Date of Patent: Jan. 31, 2023

(54) PLATELET CONCENTRATE FOR INCREASE OF CELL REGENERATION AND CELL GROWTH

(71) Applicant: Edvin Turkof, Vienna (AT)

(72) Inventors: Markus Dettke, Vienna (AT); Arthur Adler, Vienna (AT)

( * ) Notice: Subject to any disclaimer, the term of this patent is extended or adjusted under 35 U.S.C. 154(b) by 464 days.

(21) Appl. No.: 15/544,876

(22) PCT Filed: Jan. 21, 2016

(86) PCT No.: PCT/EP2016/051235
§ 371 (c)(1),
(2) Date: Jul. 19, 2017

(87) PCT Pub. No.: WO2016/116560
PCT Pub. Date: Jul. 28, 2016

(65) Prior Publication Data
US 2018/0021377 A1   Jan. 25, 2018

(30) Foreign Application Priority Data

Jan. 21, 2015   (EP) .................................... 15151913

(51) Int. Cl.
A61K 35/16 (2015.01)
A61K 8/98 (2006.01)
A61Q 5/00 (2006.01)

(52) U.S. Cl.
CPC .............. *A61K 35/16* (2013.01); *A61K 8/983* (2013.01); *A61Q 5/002* (2013.01)

(58) Field of Classification Search
CPC ........ A61K 35/16; A61K 35/35; A61K 35/19; A61L 27/54; A61L 27/36
See application file for complete search history.

(56) References Cited

U.S. PATENT DOCUMENTS 8,105,580 B2 * 1/2012 Fraser ..................... A61K 35/12
424/93.7
2014/0127314 A1   5/2014 Copland et al.

FOREIGN PATENT DOCUMENTS

| CN | 102058905 A | 5/2011 | | |
|---|---|---|---|---|
| JP | 2014030663 A | 2/2014 | | |
| WO | 2013/007308 A1 | 1/2013 | | |
| WO | WO-2013003356 A1 * | 1/2013 | ............ | C12N 5/0668 |
| WO | WO-2013113024 A1 * | 8/2013 | ............. | A61K 35/19 |
| WO | 2014/027362 A1 | 2/2014 | | |
| WO | 2014/027363 A1 | 2/2014 | | |

OTHER PUBLICATIONS

Roffi et al. BioMed Research International. 10 pages (Year: 2014).*
Fekete et al. Cytotherapy. May 2012; 14(5): 540-554. (Year: 2012).*
Matsubara et al. Biochemical and Biophysical Research Communications 378 (2009) 716-720. (Year: 2009).*
Pais et al. Am J Physiol Gastrointest Liver Physiol 307: G330-G337, 2014. Specifically, p. G330 (Year: 2014).*
Cervelli et al, "P.R.L. Platelet Rich Lipotransfert: Our Experience and Current State of Art in the Combined Use of Fat and PRP", Biomed Res Int, Article ID 434191 (2013). doi:10.115/2013/434191.
Cervelli et al, "The Effect of Autologous Activated Platelet Rich Plasma (AA-PRP) Injection on Pattern Hair Loss: Clinical and Histomorphometric Evaluation", Biomed Res. Int., Article ID 760709 (2014). doi:10.1155/2014/760709.
Fekete et al, "Platelet lysate from whole blood-derived pooled platelet concentrates and apheresis-derived platelet concentrates for the isolation and expansion of human bone marrow mesenchymal stromal cells: production process, content and identification of active components", et al. Cytotherapy, 2012, 14:540-554.
Kang et al, "The effect of CD34+ cell-containing autologous platelet-rich plasma injection on pattern hair loss: a preliminary study", J. Eur. Acad. Dermatol. Venereol., 2014, 28:72-79.
Lee et al, "Therapeutic efficacy of autologous platelet-rich plasma and polydeoxyribonucleotide on female pattern hair loss", Wound Repair Regen. 23:30-36, 2015.
Pires Fraga et al, "Increased survival of free fat frafts with platelet-rich plasma in rabbits", J. Plastic. Reconstructive & Aesthetic Surgery, 2010, 63, e818-e822.
Murphy et al, "Adult and umbilical cord blood-derived platelet-rich plasma for mesenchymal stem cell proliferation, chemotaxis, and cryo-preservation", Biomaterials, 2012, 33:5308-5316.
Schiavone et al, "Platelet-Rich Plasma for Androgenetic Alopecia: A Pilot Study", Dermatol. Surg. 40:1010-1019, 2014.
Schlenke, Peter "Pathogen Inactivation Technologies for Cellular Blood Components: an Update", 2014, Transfus. Med. Hemother., 41:309-325.
Sclafani, Anthony "Platelet-Rich Fibrin Matrix (PRFM) for Androgenetic Alopecia", Facial Plast. Surg. 30:219-224, 2014.
Takikawa et al, "Enhanced Effect of Platelet-Rich Plasma Containing a New Carrier on Hair Growth", Dermatol. Surg. 37:1721-1729, 2011.
International Search Report for PCT/EP16/51235 dated Mar. 22, 2016; 6 pages.
Written Opinion of the ISA for PCT/EP16/51235 dated Mar. 22, 2016; 8 pages.
International Preliminary Report on Patentability for PCT/EP16/52135 dated Jul. 25, 2017; 9 pages.
Extended European Search Report for EP15151913.9 dated Apr. 13, 2015; 8 pages.
European Directorate for the Quality of Medicines & Healthcare, European Council, "Guide to the preparation, use and quality assurance of blood components," chapter 5, pp. 326-327 (2017).

\* cited by examiner

*Primary Examiner* — Amy L Clark
(74) *Attorney, Agent, or Firm* — Loza & Loza, LLP; Michael Fedrick

(57) ABSTRACT

The invention refers to a decomposed platelet concentrate containing ≤50% intact platelets and optionally ≥200 pg/ml RANTES and specifically to its use in the prevention or treatment of hair loss and/or for promoting hair growth. The invention further refers to a composition comprising the decomposed platelet concentrate and body fat cells and the use of said composition for reconstructive and aesthetic and curative surgery and pain relief treatment.

5 Claims, No Drawings

PLATELET CONCENTRATE FOR INCREASE OF CELL REGENERATION AND CELL GROWTH

CROSS-REFERENCE TO RELATED APPLICATIONS

This application is the U.S. national stage of International Patent Application No. PCT/EP2016/051235, filed on Jan. 21, 2016 and entitled PLATELET CONCENTRATE FOR INCREASE OF CELL REGENERATION AND CELL GROWTH, which claims the benefit of priority under 35 U.S.C. § 119 from European Patent Application No. 15151913.9, filed Jan. 21, 2015. The disclosures of the foregoing applications are incorporated herein by reference in their entirety.

FIELD OF THE INVENTION

The invention refers to a decomposed platelet concentrate containing ≤50 intact platelets and optionally ≥200 pg/ml RANTES and specifically to its use in the prevention or treatment of hair loss and/or for promoting hair growth. The invention further refers to a composition comprising the decomposed platelet concentrate and body fat cells and the use of said composition for reconstructive and aesthetic and curative surgery and pain relief treatment.

BACKGROUND OF THE INVENTION

Whole blood is made up of various cellular components such as red cells, white cells and platelets suspended in its liquid component, plasma. Whole blood can be separated into its constituent components (cellular or liquid), and one separated component can be administered to a patient in need of that particular component.

Platelets or thrombocytes are blood cells that play a critical role in wound healing and in the generation of new tissue. Platelets promote the formation of blood clots and they act as a physical barrier at the site of rupture of a blood vessel, thereby preventing infection and avoiding further blood loss. Additionally, platelets and the proteins and peptides therein have the capacity to stimulate angiogenesis (formation of new blood vessels) and increase collagen formation, cell division and cell growth.

Enriched platelet concentrates, i.e. serum containing more platelets/μl compared to normal blood, are known to possess advantages in wound healing and formation of new tissue. The use of platelet rich plasma (PRP) in surgical sites has been shown to rapidly enhance both hard and soft tissue regeneration and repair.

PRP has attracted attention to several medical fields because of its ability to promote wound healing and formation of new tissue. In the field of hair restoration, existing evidence demonstrates PRP therapy as a promising treatment option to promote hair growth.

While PRP is in the early stages of scientific research in hair restoration, according to the state of the art, PRP is at present not meant to replace current therapies such as DHT blockers and Minoxidil but rather to complete it when it failed or showed to be insufficient.

The platelets in PRP or platelet concentrates have granules that contain a multitude of growth factors (e.g., PDGF, TGF-β, and others), which aid in accelerating angiogenesis (wound healing), osteogenesis (bone growth) and cartilage restoration. PRP/platelet concentrate, when combined with thrombin, may also be used adjunctively to control bleeding (hemostasis), to seal wounds, and as a vehicle for the delivery of drugs and/or biological agents. Further, the handling characteristics of certain organic materials, such as bone powder, can be improved by combining them with PRP/platelet concentrate, with or without the addition of thrombin. Such a combination also provides more secure placement of organic materials. Some properties of PRP/platelet concentrate and thrombin (e.g., hemostasis and wound sealing) are similar to those of fibrin glue, except that fibrin glue has a greater adhesive property because of its concentration of fibrinogen above baseline levels.

PRP has also attracted attention to plastic surgery and dermatology because of its potential use during various aesthetic procedures, reconstructive surgery and regenerative procedures like breast reconstruction, breast augmentation, various lipophilling procedures, skin-rejuvenating procedures and hair restorations.

Hair loss or baldness is technically known as alopecia and is a loss of hair from the head or body. Baldness can refer to general hair loss or androgenic alopecia (male pattern baldness). Some types of baldness can be caused by alopecia areata, an autoimmune disorder. The extreme forms of alopecia areata are alopecia totalis, which involves the loss of all head hair, and alopecia universalis, which involves the loss of all hair from the head and the body.

Baldness and hypotrichosis can have many causes, including fungal infection (tinea capitis), traumatic damage, such as by compulsive pulling (trichotillomania), as a result of radiotherapy or chemotherapy, and as a result of nutritional deficiencies such as iron, and as a result of autoimmune phenomena, including alopecia areata and hair loss associated with systemic lupus erythematodus.

Androgenic alopecia, a hereditary and androgen-dependent progressive thinning of the scalp hair in a defined pattern, is a common dermatological disorder affecting more in men and occasionally in women, with significant negative impact on their social and psychological well-being. It commonly begins by 20 years of age and affects nearly 50% of men by the age of 50 years. Its etiopathogenesis is mainly androgen-dependent and modulated via the testosterone metabolite dihydro-testosterone, the expression of hair follicle-related androgen receptor; and genetic factors also have been implicated.

PRP has also shown to be a useful adjunct to fat for enhancing the take of lipofilling, specifically in aesthetic and reconstructive surgery. Autologous fat grafting enables repair and augmentation of soft tissues and is increasingly used in surgery. Autologous fat tissue is been considered to be an ideal filler for augmentation of soft tissue, because it is biocompatible, versatile, natural-appearing, non-immunogenic, inexpensive and readily obtainable. The main limitation of fat grafting is its unpredictable take. One approach for take-enhancement is to mix the fat graft with PRP before transplantation, however quite large amounts of PRP are needed. Specifically, state of the art procedures recommend at least 20% of PRP to be added to the transplanted fat in order to achieve the best possible enhancement of the take. This may lead to high discomfort for patients who need to repeatedly undergo blood donations for PRP enrichment if more than 100 ml of fat are to be grafted.

Murillo et al. (J. Plastic. Reconstructive & Aesthetic Surgery, 2010, 63, e818-e822) describes the use of platelet rich plasma for increased survival of fat grafts in rabbits. Therein an ideal concentration of platelets in platelet rich plasma is recommended to be at least 1 mio platelets/μl.

Cervelli V. et al recommends even 40% of PRP to be added to fat (Biomed Res Int. 2013, 2013, 43491, 10.1155/2013/434191).

Most commonly, platelets are collected by continuously or intermittently introducing whole blood from a donor into a centrifuge chamber wherein the whole blood is separated into its constituent components, including platelets, based on the densities of the different components. In the separation of platelets, sometimes referred to as plateletpheresis or thrombozytapheresis, the platelets are often concentrated to form a layer of packed platelets with some residual plasma.

Fekete N. et al. (Cytotherapy, 2012, 14, 540-554) report platelet lysate from whole blood-derived pooled platelet concentrates for expansion of bone marrow mesenchymal stromal cells. It is further disclosed that high platelet content is mandatory for successful application.

For storage and/or transfusion to the patient, it is always pointed out that the platelet concentrate must be resuspended in liquid medium such as plasma and that platelets should not be frozen to avoid platelet lysis.

WO2014027362A1 and WO2014027363A1 describe growth factor concentrates from human platelets free of cellular debris which can be used for treatment of hair loss.

Murphy B. M. et al. (Biomaterials, 2012, 33, 5308-5316) report the use of platelet-rich plasma for stem cell proliferation.

Thus there is a constant need for providing optimized platelet concentrates that can be used for aesthetic and reconstructive treatments, specifically for the treatment of hair loss, and in plastic surgery which can overcome the disadvantages of the presently available platelet rich plasma or platelet concentrates. Further there is a further need in providing sufficient amounts of optimal concentrations and amounts of platelet rich plasma as the actual approaches implicate the loss of considerable volumes of blood.

SHORT DESCRIPTION OF THE INVENTION

It is the objective of the present invention to provide a new platelet concentrate and new uses thereof.

The objective is solved by the subject matter of the present application.

According to an embodiment of the invention, the inventors provide a new decomposed platelet concentrate which is a platelet concentrate of autologous or allogeneic origin containing ≤50% intact platelets and preferably ≥200 pg/ml RANTES.

Specifically, the platelet concentrate is unfiltered concentrate, thus no filtration for removal of cellular debris and/or sterile filtration is performed during production process.

According to a further embodiment of the invention, the platelet concentrate is free of isotonic medium or electrolyte isotonic solutions.

Said platelet concentrate is preferably free of thrombin or any other platelet activators.

According to a specific embodiment, said decomposed platelet concentrate is obtained by freeze thawing of a platelet fraction, thereby getting a platelet concentrate wherein more than 50% of the platelets are destroyed due to the freeze-thawing process, specifically containing ≤40%, specifically ≤30%, specifically ≤20% specifically ≤10% intact platelets, specifically ≤1% intact platelets.

In a specific embodiment, the platelet concentrate is free of intact platelet cells.

According to the invention, the source of the platelet concentrate is a platelet containing fraction which is preferably obtained from an apheresis fraction, specifically from a thrombocytapheresis or plateletpheresis fraction or of synthetic origin.

According to an alternative source, synthetic or semi-synthetic platelet or platelet substitute concentrates can be used for the present invention.

The invention also specifically provides a platelet concentrate that is formulated as a balm, solution, suspension, emulsion, ointment, foam, past, gel, cream, lotion, powder or salve.

According to an embodiment, the invention provides the inventive platelet concentrate for the preparation of a medicament, specifically for use in the stimulation of cell growth, cell regeneration or tissue regeneration.

The inventors have also shown that platelet concentrates which have been frozen and thawed or treated otherwise to reduce the number of intact platelet cells can be used for the treatment of hair loss and for increasing the survival and take of grafted fat, specifically in aesthetic and reconstructive surgery.

They have also shown that this approach can be successfully implemented because the beneficial effect of PRP in aesthetic and reconstructive procedures is not due to intact and functioning thrombocytes but may be due to the growth factors or any other proteins or polypeptides they contain.

According to the invention a decomposed, specifically unfiltered platelet concentrate is provided containing ≤50% intact platelets for use in the prevention or treatment of hair loss and/or for promoting hair growth.

According to an embodiment of the invention, hair loss can be cicatricial or non cicatricial hair loss, alopecia, androgenic alopecia, alopecia areata.

According to a further embodiment of the invention, the platelet concentrate can be used for the prevention or treatment of hair thinning and/or regenerating the hair bulb cells and/or scalp.

According to yet a further embodiment, the platelet concentrate is administered topically, intra- or subdermally, specifically via needles or microneedles.

In a further embodiment, the platelet concentrate is administered repeatedly.

The present invention had also surprisingly shown that the inventive platelet concentrates can be used in the field of lipofilling for aesthetic and reconstructive purposes.

The present invention thus also provides a novel composition comprising a decomposed platelet concentrate containing ≤50% intact platelets admixed with isolated body fat cells. Specifically, the concentrate and the fat cells are of the same origin, i.e. the same donor. Specifically, said composition is of autologous origin.

According to a specific embodiment, the fat cells are from the lipoaspirate.

The optimal volume ratio of fat cells and platelet concentrate can be determined by any skilled person, preferably the volume ratio is between 10:1 and 2:1, specifically at least 5:1 to 3:1.

According to the invention there is also provided an enriched fat graft comprising a composition according to the invention.

According to a further embodiment, the composition of the invention and/or the enriched fat graft are for use in aesthetic and reconstructive surgery.

The invention also provides a method for producing a decomposed platelet concentrate as described above, comprising the steps of freezing a platelet containing fraction free of any cryoprotective agent and/or free of isotonic medium at about −10° C., specifically at about −15° C., specifically at about −20° C., specifically at about −25° C., specifically at about −30° C., specifically at about −35° C., more specifically −40° C., optionally in the presence of an anticoagulant and optionally storing the frozen platelet concentrate for about several hours up to one or more years;

thawing said fraction at room temperature and optionally repeating the freeze thawing process until at least 50%, specifically at least 80%, more specifically at least 90% of the platelets are destroyed.

The invention also provides a method for aesthetic and/or reconstructive breast surgery, wherein the inventive composition or the enriched fat graft is administered to a patient in need thereof to augment breast volume or for any other applications of reconstructive surgery wherein fat cells are administered, for example volumetric reconstructions or aesthetic corrections in the face or any other regions of the patient's body.

According to a further embodiment of the invention, the composition or enriched fat graft of the invention is administered repeatedly.

The invention also provides a method for providing consistent enriched fat graft of constant compounding, wherein 50-300 ml of the inventive composition are filled in a storage device and stored under appropriate conditions.

DETAILED DESCRIPTION OF THE INVENTION

A decomposed platelet concentrate containing ≤50% intact platelets and preferably a content of ≥200 pg/ml RANTES is provided by the present invention.

The terms "platelet concentrate" as encompassed herein means any platelet or thrombocyte concentrate or platelet or thrombocyte fraction, wherein at least 50%, preferably at least 60%, preferably at least 70%, preferably at least 80%, preferably at least 90%, preferably at least 95%, preferably more than 95% of the platelets are destroyed or lysed, either by chemical or non-chemical methods.

According to a specific embodiment, the decomposed platelet concentrate is free of intact platelets, specifically containing platelet lysates and their respective cellular polypeptides and proteins.

Thus, the inventive platelet concentrate contains <50%, specifically ≤40%, specifically ≤30%, specifically ≤20%, specifically ≤10% intact platelets, specifically ≤1% intact platelets.

The term "free of intact platelets" according to the invention means that at least 99%, specifically 99.5%, specifically more the 99.9% of the platelets are destroyed. Therefore the term free of intact platelets is defined by containing <1%, specifically <0.5%, specifically <0.1%, specifically <0.01% intact platelets.

In a further embodiment, the platelet concentrate contains at least 200 pg/ml RANTES (CCL5).

According to a further embodiment, the platelet concentrate contains increased amounts of other growth factors, for example EGF, VEGF, PDGF, transforming growth factor β1.

Specifically, the inventive platelet concentrate further contains at least one growth factor selected from the group of PDGF-AB, PDGF-BB, PDGF-AA, epidermal growth factor (EGF), vascular endothelia growth factor (VEGF), basic fibroblast growth factor (bFGF), Rantes (CCLS), transforming growth factor ß (TGF-ß), granulocyte colony-stimulating factor (GCSF), granulocyte macrophage colony-stimulating factor (GMCSF), Interferon gamma (IFN-γ), tumor necrosis factor alpha (TFN α), interleukin 1 alpha (IL-1α), interleukin 1 beta (IL-1β), interleukin 2 (IL-2), interleukin 6 (IL-6), interleukin 7 (IL-7), interleukin 8 (IL-8), interleukin 19 (IL-10), macrophage inflammatory protein 1 alpha (MIP-1α), macrophage inflammatory protein 1 beta (MIP-1β), cluster of differentiation 40 (CD40L), vascular cell adhesion molecule 1 (VCAM-1), intercellular adhesion molecule 1 (ICAM1, CD54), chemokine ligands, e.g. CXC ligand, C—C ligands.

According to a specific embodiment the inventive platelet concentrate contains PDGF-AB/BB in an amount of 200.000-600.000 pg/ml.

According to a specific embodiment the inventive platelet concentrate contains PDGF-AA in an amount of 150.000-250.000 pg/ml.

According to a specific embodiment the inventive platelet concentrate contains EGF in an amount of 1000-1300 pg/ml.

According to a specific embodiment the inventive platelet concentrate contains VEGF in an amount of 100-250 pg/ml.

According to a specific embodiment the inventive platelet concentrate contains bFGF in an amount of 100-500 pg/ml.

According to a specific embodiment the inventive platelet concentrate contains Rantes in an amount of 2×10 log6-3.10 log6 pg/ml. According to a specific embodiment the inventive platelet concentrate contains TGF-β in an amount of 50.000-150.000 pg/ml.

According to a specific embodiment the inventive platelet concentrate contains IFN gamma in an amount of 10-20 pg/ml.

According to a specific embodiment the inventive platelet concentrate contains GCSF in an amount of 50-100 pg/ml.

According to a specific embodiment the inventive platelet concentrate contains GMCSF in an amount of 15-55 pg/ml, specifically 18-50 pg/ml.

According to a specific embodiment the inventive platelet concentrate contains TFN alpha in an amount of 5-12 pg/ml, specifically 6-10 pg/m. According to a specific embodiment the inventive platelet concentrate contains IL-1α in an amount of 30-50 pg/ml, specifically 35-47 pg/ml.

According to a specific embodiment the inventive platelet concentrate contains IL-1β in an amount of 0.5-6 pg/ml, specifically 1-5 pg/ml.

According to a specific embodiment the inventive platelet concentrate contains IL-6 in an amount of 1-5 pg/ml.

According to a specific embodiment the inventive platelet concentrate contains IL-7 in an amount of 15-50 pg/ml, specifically 30-47 pg/ml.

According to a specific embodiment the inventive platelet concentrate contains IL-8 in an amount of 70-90 pg/ml, specifically 74-86 pg/ml.

According to a specific embodiment the inventive platelet concentrate contains IL-10 in an amount of 0.5-6 pg/ml, specifically 1-5 pg/ml.

According to a specific embodiment the inventive platelet concentrate contains MIP-1α in an amount of 250-400 pg/ml, specifically 290-360 pg/ml.

According to a specific embodiment the inventive platelet concentrate contains MIP-1β in an amount of 30-60 pg/ml, specifically 43-51 pg/ml.

According to a specific embodiment the inventive platelet concentrate contains CD40L in an amount of 21000-40000 pg/ml, specifically 21350-38100 pg/ml.

According to a specific embodiment the inventive platelet concentrate contains VCAM-1 in an amount of 600000-3000000 pg/ml, specifically 690000-2897000 pg/ml.

According to a specific embodiment the inventive platelet concentrate contains ICAM-1 in an amount of 40000-250000 pg/ml, specifically 43000-231000 pg/ml.

According to a specific embodiment the inventive platelet concentrate contains CXC ligand in an amount of 4000-20000 pg/ml, specifically 4600-17600 pg/ml.

The term "autologous origin" means that the concentrate is derived from a platelet fraction that is isolated from a single donor, either based on one or more donation(s). Preferably, the platelet concentrate is obtained in one single collection process or in few collection processes and is stored for single or repeated administration. In the autologous setting the donor and the patient is the same person.

According to a preferred embodiment, the platelet concentrate is of autologous origin.

The term "allogenic origin" means that the concentrate is derived from a platelet fraction that is isolated from a healthy donor or is derived from a pool of donors. The concentrate is applied to a person/patient who is not the donor. Preferably, the platelet concentrate is obtained from one single donor during a single collection process.

The term "synthetic origin" means that the concentrate is produced synthetically, i.e. originating from synthetic platelet substitutes.

Said platelet rich fraction useful as source material for the inventive decomposed platelet concentrate can be, but is not limited to whole blood, platelet rich plasma or otherwise concentrated blood.

The decomposed platelet concentrate according to the invention specifically originates from or is derived from any platelet rich fraction originally containing at least 150000, specifically >200000 intact blood platelets/µl, specifically >500000 intact blood platelets per µl, preferably $>1.10^6$/µl.

In a specific embodiment, the platelet rich fraction is obtained from an apheresis fraction, specifically from a thrombocytapheresis or plateletpheresis or plasmapheresis fraction.

Virus inactivation of the platelet rich fraction used as source material may be performed by any method known for plasma or whole blood virus inactivation, which may be, but is not restricted to solvent-detergent (SD) treatment addition of methylene blue (MB), UV treatment, treatment with psoralen, e.g. psoralen S-59, addition of vitamin B2 and broad-spectrum UV light, narrow-bandwidth UV-C light (Schlenke P, 2014, Transfus. Med. Hemother., 41, 309-325).

According to the invention, platelet lysis can be performed using any chemical or non-chemical method known by the skilled person. Non-chemical treatment for platelet/cell lysis is preferred, including, but not limited to methods of freeze-thawing, sonication, lyophilization, French press usage, heat treatment, hypotonic shock or nitrogen cavitation.

Freeze-thawing of the platelet source is preferred.

According to a preferred method, a platelet containing fraction is frozen at a temperature of at least −10° C., specifically at least −25° C., specifically at least −30° C., specifically at least −35° C., preferably in the absence of any cryoprotectant, for a sufficient time period needed for cell lysis, specifically for at least 15 minutes, specifically at least 20 minutes, specifically at least 30 minutes, specifically at least 45 minutes, specifically 1 hour, specifically for at least 1.5 hours, specifically for at least 2 hours. Specifically, the freezing temperature is higher than −120° C., specifically higher than −85° C., specifically higher than −80° C., specifically it is up to −80° C., −70° C., -60° C., −50° C., −40° C., −35° C., −30° C.

Freezing is followed by a thawing process at room temperature, specifically at 25° C., more specifically at about 27.5° C., specifically at about 30° C., specifically at about 35° C., specifically at about 37.5° C.

According to a specific embodiment, the platelet fraction is repeatedly treated by freeze-thawing cycles, specifically said cycles can be repeated two times, three-times, four-times, five-times or more until the desired lysis of platelets is reached.

Specifically said platelet concentrate is free from any platelet activators, e.g. from thrombin, $CaCl_2$ and other additives like trehalose.

Specifically, the inventive platelet concentrate does not undergo further filtration.

Specifically, the platelet concentrate is free from isotonic buffer or electrolyte isotonic medium.

More specifically, the platelet concentrate is free of NaCl, sodium gluconate, sodium acetate trihydrate, KCl, magnesium chloride, human serum albumin.

The platelet concentrate according to the invention can be of any structure or consistency applicable to the respective need. Specifically, such concentrate can be applied to the surface or a wound of an individual in the form of a layer, such as a gel, a cream or a paste or it can be applied directly in a liquid form, e.g. by aspiration.

Alternatively it can be formulated as a balm, suspension, emulsion, ointment, foam, paste or lotion.

The invention also provides said platelet concentrate for the preparation of a medicament.

The inventive platelet concentrate may be used in the stimulation of hair growth, hair thickening, cell growth, cell regeneration or tissue regeneration or enhance the take of lipofilling.

A method for producing the inventive decomposed platelet concentrate comprises the steps of
  freezing a platelet containing fraction, optionally in the presence of an anticoagulant and
  optionally storing the frozen platelet concentrate;
  thawing said fraction.

An alternative method for producing the inventive decomposed platelet concentrate comprises the steps of
  freezing a platelet containing fraction at about −25° C., optionally in the presence of an anticoagulant for at least 30 minutes and
  optionally storing the frozen platelet concentrate for about several hours/days/years;
  thawing said fraction at room temperature for about 30 minutes.

Optionally the platelet concentrate can be treated by methods known for concentrating the respective platelet lysate compounds. Said method can be for example filtration or centrifugation.

Production of the platelet concentrate is to be performed under sterile conditions.

For further purification, the platelet concentrate may also be treated by virus inactivation.

In case of using synthetic or autologous platelet concentrates, virus removal methods may not be necessary.

The platelet concentrate may also be stored at freezing conditions for several days, weeks, months or years.

A further aspect of the invention is a novel method for prevention or treatment of hair loss and/or for promoting hair growth using the inventive decomposed, platelet concentrate of autologous origin containing ≤50% intact platelets.

The decomposed platelet concentrate can be administered as single application or repeatedly.

The decomposed platelet concentrate of the invention can be, for example, administered to the scalp every one, two, three to four months or any other desired intervals. Alternatively, the decomposed platelet concentrate can be applied before or during surgery to ensure successful autologous hair graft survival.

The inventive concentrate can also be used for natural stimulation of thinning hair.

The decomposed autologous platelet concentrate contains platelet lysate that may cause growth of the hair by stimulating the stem cells located in the dermal papilla as well as other structures of the hair follicle. These lysates promote healing, accelerate the rate and degree of tissue healing and regeneration, response of the body to injury, and induction of new cellular growth. The primary purpose of using the autologous decomposed platelet concentrate in hair restoration is to stimulate inactive or newly implanted hair follicles into an active growth phase.

Hair follicle has a very complex biologic structure and growth of the hair process is regulated by specific growth cycles. The mature follicle undergoes successive transformation from anagen, active hair shaft production, to catagen (apoptosis-driven regression) to telogen, resting phase with the involution of hair follicle. Role of apoptosis, by the pathway of caspases cascade, in determining the passage from anagen to catagen is well known. Many growth factors play a fundamental role in the life-long cyclic transformation of the hair follicle functioning as biologic switches that are turned on and off during the different phases, controlling the active phase and promoting apoptosis to induce catagen and telogen. The main growth factors involved in the establishment of hair follicle are vascular endothelial growth factor (VEGF), epidermal growth factor (EGF), insulin 1-like growth factor, and fibroblast growth factor (FGF). Platelet lysates contain large amounts of platelet-derived growth factor (PDGFAA, PDGF BB, and PDGF AB), transforming growth factor beta (TGFβ1 and β2).

The use of the inventive decomposed platelet concentrate may increase the proliferation of dermal papilla cells and stimulated extracellular signal regulated kinase and Akt signaling. The beneficial effects of the decomposed platelet concentrate may be attributed to various platelet-derived growth factors causing improvement in the function of hair follicle and promotion of hair growth, while avoiding increased blood loss and in the absence of repeated blood donations for each single treatment. A further beneficial effect of the inventive platelet concentrate may be due to the balanced presence of components originating from the platelet rich fraction which are not specifically removed by filtration or any other treatment besides freezing and thawing.

Specifically, the decomposed platelet concentrate can be used in the prevention or treatment of any type of hair loss, either hereditary or non-hereditary hair loss, for example cicatricial or non cicatricial hair loss, alopecia, androgenic alopecia, alopecia areata, hypotrichosis.

It can also be used for prevention or treatment of hair thinning and/or regenerating the hair bulb cells and/or scalp.

The platelet concentrate can be administered topically, intra- or subdermally or via needles, for example microneedles. It may be administered via nappage technique, i.e. multiple, small injections in a linear pattern one cm apart under aseptic conditions.

According to a further method, the scalp is stimulated to activate the wound healing process subsequent to autologous hair graft. Topical anesthesia can be applied on the portion of the scalp where decomposed platelet concentrate will be injected. Additionally to the injection of the inventive platelet concentrate, a micro needling roller device can be used. The roller uses about 200 very fine needles to pierce the epidermis creating micro wounds thereby stimulating collagen formation. Further to the injection, the inventive platelet concentrate is then additionally administered to the microneedled area. The resulting 'micro-channel effect' also helps to infuse the platelet concentrate into the area thereby increasing the effectiveness.

The volume of decomposed platelet concentrate to be administered in a single application varies with regard to the surface of the area, specifically it may be between less than 5 ml to more than 15 ml.

According to established methods in aesthetic and reconstructive breast surgery and other reconstructive and aesthetic procedures of the body, the decomposed platelet concentrate is combined with fat cells shortly before administration. The decomposed platelet concentrate has been shown to be a useful adjunct to fat for enhancing the take of lipofilling.

By using this method, the patient does not need to undergo repeated blood or plasma donations but a decomposed autologous platelet concentrate is provided that is of consistent quality and sufficient quantity which can be stored under freezing conditions and can be thawed and administered upon surgical need repeatedly without any negative side effects.

A concentration of platelet rich concentrate of around 1:5 compared to normal plasma, and a volume ratio of decomposed platelet concentrate to fat of 1:3 to 1:5, specifically up to 1:10 according to the respective need.

To actually manufacture PRP, numerous kits emerged from various medical suppliers. All of them are characterized by the fact that blood is taken from the patient, centrifuged and then the lower part of the obtained plasmacylinder is used to enrich the fat, while the concentrated erythrocytes, and most often—according to the rules of the respective physician—also the buffy coat, are to be discarded. Given the fact that with any of the existing kits the amount of PRP that can be obtained from 10 ml blood varies between 1-3 ml, effective PRP enrichment can only be done for small amounts of fat transplantation. PRP enrichment is therefore still limited for aesthetic procedures in the face where 1) small amounts of fat are enough to reach the desired volume enhancement at the recipient site and 2) small amounts of PRP are enough to enrich this small amount of fat with the actually recommended concentration and volume ratio.

For aesthetic breast augmentation, however, 200-350 ml of fat per side are necessary and thus PRP enrichment is practically impossible, as one would need around 100 ml PRP for 500 ml of autologous fat. To produce 100 ml PRP with the available kits, 500-1000 ml of blood are necessary, and this volume loss cannot be tolerated for patients undergoing surgery.

The inventors surprisingly have found a way to produce a large volume platelet concentrate of advantageous efficacy and tolerability which may be produced at any desired concentration without having to waste a single erythrocyte and with constant quality and composition which can be provided portion-wise.

Thus, a further aspect of the invention is a novel composition comprising a decomposed platelet concentrate, specifically of autologous origin containing ≤50% intact platelets in combination with isolated body fat cells originated from the same individual.

Adipose tissue or body fat is a loose connective tissue composed mostly of adipocytes. In addition to adipocytes, adipose tissue contains the stromal vascular fraction (SVF) of cells including preadipocytes, fibroblasts, vascular endothelial cells and a variety of immune cells (i.e. adipose tissue macrophages (ATMs)). Adipose tissue is derived from preadipocytes. Its main role is to store energy in the form of lipids, although it also cushions and insulates the body. The two types of adipose tissue are white adipose tissue (WAT) and brown adipose tissue (BAT).

Specifically, the used autologous body fat cells used for the present invention are from the lipoaspirate gained through liposuction procedure. Lipoaspirates are abundant stem cell sources; adipose (fat) stem cells can be retrieved in high numbers from liposuction aspirates.

The weight ratio of fat cells and platelet concentrate is preferably between 10:1 and 2:1, specifically between 8:1 and 2.5:1, more specifically between 6:1 and 3:1, more specifically between 5:1 and 3:1.

Said combination of fat cells and decomposed platelet concentrate can also be used for providing an enriched fat graft.

According to the invention, the term enriched fat graft encompasses a mixture of the platelet concentrate of the invention and fat cells, optionally washed with aqueous solution, specifically body fat cells. The ratio of fat cells and platelet concentrate is between 10:1 and 2:1, specifically 10:1, 9:1, 8:1, 7:1, 6:1, 5:1, 4:1, 3:1, 2:1.

Washing of body fat cells isolated from the patient can be performed by any buffer or aqueous solution, e.g. saline solution, specifically to remove blood cells.

The inventive composition has been successfully shown to be highly advantageous when used in reconstructive and aesthetic procedures, specifically in surgery wherein high amounts of fat cells are needed for reconstitution, specifically in breast surgery or when repeated, painful and time consuming blood donations are not desired.

Therefore the invention provides a highly advantageous method for reconstructive and aesthetic breast surgery, wherein the inventive composition or enriched fat graft comprising said composition is administered to a patient in need thereof to augment breast volume and also a highly advantageous method for any kind of lipofilling procedures when repeated applications are needed.

Specifically, the inventive composition can also be used for pain relief treatment, wherein the composition is administered to a site of an area wherein tissues have been removed by surgical methods or scars.

Said administration can be a single administration, or a repeated administration.

The composition may be filled into bags, syringes or any other appropriate storage device and stored for repeated use, specifically to provide composition of identical or similar content.

Specifically, a method for providing consistent enriched fat graft of constant compounding is encompassed, wherein 50-300 ml or more of the composition are filled into storage devices.

The invention furthermore comprises the following items:

1. Decomposed platelet concentrate containing ≤50% intact platelets and ≥200 pg/ml RANTES.
2. The platelet concentrate according to item 1, wherein said concentrate is of autologous, allogenic or synthetic origin.
3. The platelet concentrate according to item 1 or 2, wherein the decomposed platelet concentrate is obtained by freeze thawing of a platelet fraction.
4. The platelet concentrate according to item 1 to 3, wherein the platelet fraction is obtained from an apheresis fraction, specifically from a thrombocytapheresis fraction.
5. The platelet concentrate according to any one of items 1 to 4, wherein the platelet concentrate contains ≤40%, specifically ≤30%, specifically ≤20%, specifically ≤10% intact platelets, specifically ≤1% intact platelets.
6. The platelet concentrate according to any one of items 1 to 5, wherein the platelet concentrate is free of intact platelets.
7. The platelet concentrate according to items 1 to 6, wherein the platelet concentrate is formulated as a balm, solution, suspension, emulsion, ointment, foam, past, gel, cream, lotion, powder or salve.
8. The platelet concentrate according to any one of items 1 to 7 for the preparation of a medicament.
9. The platelet concentrate according to items 1 to 8 for use in the stimulation of cell growth, cell regeneration or tissue regeneration.
10. A decomposed platelet concentrate containing ≤50% intact platelets for use in the prevention or treatment of hair loss and/or for promoting hair growth.
11. The platelet concentrate for use according to any one of items 1 to 10, wherein the hair loss is selected from the group consisting of cicatricial or non cicatricial hair loss, alopecia, androgenic alopecia, alopecia areata.
12. The platelet concentrate for use according to any one of items 1 to 11 for the prevention or treatment of hair thinning and/or regenerating the hair bulb cells and/or scalp.
13. The platelet concentrate for use according to any one of items 1 to 12, wherein the platelet concentrate is administered repeatedly.
14. The platelet concentrate for use according to any one of items 10 to 13, wherein the platelet concentrate is administered topically, intra- or subdermally or via needles.
15. Composition comprising a decomposed platelet concentrate according to any one of items 1 to 7 and body fat cells.
16. The composition according to item 15, wherein the fat cells are from lipoaspirate.
17. The composition according to items 15 or 16, wherein the weight ratio of fat cells and platelet concentrate is between 10:1 and 4:1, specifically between 5:1 to 3:1.
18. The composition according to any one of items 15 to 17, wherein the body fat cells and the platelet concentrate are from the same donor.
19. Enriched fat graft comprising a composition according to any one of items 15 to 18.
20. The platelet concentrate or the composition or the enriched fat graft according to any one of items 15 to 19 for use in aesthetic and reconstructive surgery of the body, specifically in breast surgery.
21. Method for producing a decomposed platelet concentrate according to any one of items 1 to 6, comprising the steps of
    freezing a platelet containing fraction, optionally in the presence of an anticoagulant and
    optionally storing the frozen platelet concentrate;
    thawing said fraction.
22. Method for lipofilling procedure, wherein the composition according to any one of items 15 to 18 or the Enriched fat graft according to item 19 is administered to a patient in need thereof to augment volume of any desired amount at any region of the body.
23. Method for breast surgery, wherein the composition according to any one of items 15 to 18 or the enriched fat graft according to item 19 is administered to a patient in need thereof to augment breast volume 24. Method according to item 22 or 23, wherein the composition or enriched fat graft is administered repeatedly.

25. Method according to items 22 or 23, wherein the composition is an autologous composition.

26. Method for providing consistent enriched fat graft of constant compounding, wherein 50-300 ml of the composition according to item 19 is filled in storage devices.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Freeze and Thawing of Platelet Fractions for Producing Decomposed Platelet Compositions For cell lysis/brake-up the outer cell membrane the platelets are frozen and thawed. For freezing the platelet fractions, the solution is exposed at a temperature of less than −25 ° C. without the addition of any cryoprotectant and kept at a temperature of less than −25° C. for at least 2 hrs. Thawing is performed at room temperature. The freeze-thawing cycle is repeated at least twice and the cell lysis is controlled by the performance of a regular blood count on a commercial cell counter. A minimum of >80% of platelets should be lysed, otherwise the freezing/thawing cycle is repeated until the final QC parameter of >80% platelet lysis is reached. The final platelet-free supernatant can be stored at a temperature less than −25° C. until use.

Example 2

Use of Decomposed Platelet Compositions in Breast Surgery

Female patients who undergo surgery for breast cancer (partial breast removal/lumpectomy) and who are scheduled for breast reconstruction with autologous fat transfer (lipofilling) are enrolled in this pilot study. Prior to surgery, all patients are presented to the department for blood group serology and transfusion medicine to examine the eligibility for autologous PRP donation (virus load, caliber of cubital veins). If eligibility is given, admission to the hospital takes place and patients are referred to the department for blood group serology and transfusion medicine where they are linked to a cell-separator (Amicus™ from Fresenius Inc.). Within 45 minutes, 100 ml of PRP with a platelet concentration of 1:7 to peripheral blood is isolated and said fraction, divided into 10 10 ml portions and subsequently undergoes the freezing and storing procedure as descried above. At the day of surgery, the necessary volume of fat is estimated by the surgeon and the department for blood group serology and transfusion medicine is informed to thaw the frozen concentrate in the amount of a fifth of the estimated patient's transfer fat volume. Donor site is infiltrated with the semi-wet technique by ringer-lactate and 1 mg of adrenaline/500 ml. Fat removal is done by hand with a Sattler cannula (3 mm diameter, 16 holes of 1.5 mm diameter) and a vacuum of less than 0.5 bar. Next, the obtained lipoaspirate is repeatedly washed with saline solution until the majority of blood cells are eliminated. Finally the thawed concentrate is brought to room temperature, next transported into the operating room by pneumatic delivery and added to the washed fat in a ratio of 1:5 immediately thereafter, lipofilling is completed.

Results

Lipofilling enriched with PRP could be implemented in all patients with convenient veins. The amount of transferred fat varied from 90 ml to 320 ml, the volume of PRP added is a fifth, respectively. No postoperative complications occur, namely no infection, lump formation etc. All patients are expected the day before surgery, 10 days, 1 month and three months thereafter.

Example 3

Preparation of "Autologous Platelet (Thrombocyte) Concentrate (PC)"

Patient is tested to be free of viral and bacteriological infection and connected to a Cell Separator (model Amycus from Fresenius) for around 45 minutes.

250 ml of platelet concentrate (PC) are obtained and divided in small portions of 10 ml (if dedicated for hair restoration) or 40 ml (if dedicated for autologous fat and transferred) by the use of standard plastic bags.

Procedure 1

Bags are frozen at −80° and stored for 3 weeks. A small sample is thawed, tested and released. Before every surgical procedure, one bag is handed over the surgical team, and is thawed at room temperature and used immediately.

Procedure 2

Bags are shock frozen at −80° for 20 minutes, thawed and again shock frozen. A small sample is thawed, tested and released. Before every surgical procedure, one bag is handed over to the surgical team, thawed at room temperature and used immediately.

Example 4

Alopecia Treatment

Preparation of scalp

Procedure 1:

The scalp is cleansed with 70% alcohol, and local anaesthesia of 2% lidocaine with 1:100 000 epinephrine (3-5 mL) is injected on the frontal and parietal areas Procedure 2

Patient is requested to wash her/his hair with a desinfecting shampoo 2 hours prior to the intervention. Patient is sedated with Midazolma/Propofol Treatment The thawed platelet concentrated (PC) is injected intradermally; 0.1-0.2 ml/injection using a 26 cauge needle. Distance between injections: 1-1.5 cm. depending on the area for treatment, 50-200 injections are administered.

Patients are treated every 4 weeks for a total of 3-5 treatments.

A significant improvement could be seen in patients 6 months after treatment.

Example 5

Autologous Fat Grafting—Breast Reconstruction 40 ml of platelet concentrate (PC) are mixed 1:4 (v/v) with autologous fat obtained by liposuction Fat harvest is performed under full anaesthesia subsequent to instillate the donor area with a solution (1000 ml Ringer Lactate+1 mg Adrenaline) with the semi-wet technique. After waiting 10 minutes, liposuction is performed with the hand and 10 ml Luer-Lock Syringes and cannulas with diameters of 2 mm and 18 holes with diameters of 1 mm.

The lipoaspirate is centrifuged for 14 seconds at 1000-1200 g force; the fat cylinder is then transferred to a large luer Lock syringe of 60 ml; when filled to 50 ml, 10 ml of PC is added; followed by gentle and continuous mixing, the fat/PC suspension is transferred to small 5 ml Luer Lock syringes and is transferred to the breast with many passes sub-pectoral, epi-pectoral and subcutaneous locations, avoiding intraglandular application.

Depending on situation of the patient th3 procedure is repeated every 2 months, after assessment of success of the previous treatment, typically 3-4 times. A significant improvement can be seen in patients 3 month after the last treatment.

LITERATURE

Lee, S.-H. et al. Therapeutic efficacy of autologous platelet-rich plasma and polydeoxyribonucleotide on female pattern hair loss. *Wound Repair Regen.* 23,30-36 (2015).

Schiavone, G., Raskovic, D., Greco, J. & Abeni, D. Platelet-Rich Plasma for Androgenetic Alopecia: A Pilot Study. *Dermatol. Surg.* 40,1010-1019 (2014).

Cervelli, V. et al. The Effect of Autologous Activated Platelet Rich Plasma (AA-PRP) Injection on Pattern Hair Loss: Clinical and Histomorphometric Evaluation. *Biomed Res. Int* 760709 (2014). doi:10.1155/2014/760709Sclafani, A. P. Platelet-Rich Fibrin Matrix (PRFM) for Androgenetic Alopecia. *Facial Plast. Surg.* 30,219-224 (2014).

Takikawa, M. et al. Enhanced Effect of Platelet-Rich Plasma Containing a New Carrier on Hair Growth. *Dermatol. Surg.* 37,1721-1729 (2011).

Kang, J.-S. et al. The effect of CD34+cell-containing autologous platelet-rich plasma injection on pattern hair loss: a preliminary study. *J. Eur. Acad. Dermatol. VenereoL* 28,72-79 (2014).

The invention claimed is:

1. A composition comprising body fat cells and a decomposed, unfiltered platelet concentrate containing <50% intact platelets and >200 pg/ml RANTES, wherein the body fat cells and the platelet concentrate are in a volume ratio of between 10:1 and 4:1, and wherein the body fat cells are obtained by:
   removing fat tissue from a subject to obtain a lipoaspirate; and
   removing blood cells from the lipoaspirate, thereby obtaining the body fat cells.

2. The composition of claim 1, wherein the body fat cells and the platelet concentrate are from the same subject.

3. The composition of claim 1, wherein the volume ratio of body fat cells and platelet concentrate is between 5:1 and 3:1.

4. The composition of claim 1, wherein the decomposed platelet concentrate is obtained by freeze thawing of a platelet fraction.

5. The composition of claim 1, wherein the decomposed platelet concentrate is free of intact platelets.

* * * * *